US012697507B2

(12) United States Patent
 Kamerling et al.

(10) Patent No.: US 12,697,507 B2
(45) Date of Patent: Aug. 4, 2026

(54) COMPUTER-IMPLEMENTED MEDICAL METHOD FOR RADIATION TREATMENT (RT) PLANNING FOR TREATING MULTIPLE LESIONS OF A PATIENT

(71) Applicant: Brainlab SE, Munich (DE)

(72) Inventors: Cornelis Kamerling, Munich (DE); Stefan Schell, Munich (DE)

(73) Assignee: BRAINLAB SE, Munich (DE)

( * ) Notice: Subject to any disclaimer, the term of this patent is extended or adjusted under 35 U.S.C. 154(b) by 83 days.

(21) Appl. No.: 18/693,481

(22) PCT Filed: Dec. 21, 2022

(86) PCT No.: PCT/EP2022/087266
§ 371 (c)(1),
(2) Date: Mar. 19, 2024

(87) PCT Pub. No.: WO2024/132130
PCT Pub. Date: Jun. 27, 2024

(65) Prior Publication Data
US 2025/0135227 A1     May 1, 2025

(51) Int. Cl.
*A61N 5/10*          (2006.01)

(52) U.S. Cl.
CPC ........... *A61N 5/103* (2013.01); *A61N 5/1047* (2013.01)

(58) Field of Classification Search
None
See application file for complete search history.

(56) References Cited

U.S. PATENT DOCUMENTS 11,376,445 B1 *  7/2022  Adamson ............. A61N 5/1069
2021/0260405 A1   8/2021  Kamerling

FOREIGN PATENT DOCUMENTS

EP        1563799 A1    8/2005
EP        2782642 B1    3/2016
EP        3497702 B1    12/2020
(Continued)

OTHER PUBLICATIONS

"Dynamic conformal arcs-based single-isocenter VMAT technique for radiosurgery of multiple brain metastases" Medical Dosimetry, Elsevier, US, vol. 46, No. 2, Dec. 8, 2020, pp. 195-200, XP086557234, ISSN: 0958-3947, DOI: 10.1016/J.MEDDOS.2020.11.005). (Year: 2020).*

(Continued)

*Primary Examiner* — Hoon K Song
(74) *Attorney, Agent, or Firm* — Gray Ice Higdon

(57) ABSTRACT

According to the present invention, the method presented herein may determine, which lesions of a patient need modulation, and which not. In an optional step an arc setup optimization is performed for creating the RT treatment plan. Moreover, a conformal shape optimization is performed, preferably for all lesions of the patient. Furthermore, a VMAT optimization is performed with the restriction that conformal the shapes determined before must stay conformal during the VMAT optimization for subset of lesions. In this way, the benefits of conformal arcs and modulated arcs are combined by generation of treatment plans using hybrid arcs. This method allows that each arc can contain both conformal and modulated apertures.

19 Claims, 3 Drawing Sheets

(56)        References Cited

FOREIGN PATENT DOCUMENTS

EP          3817809  B1      8/2021

OTHER PUBLICATIONS

Palmiero, Allison et al., Management of Multiple Brain Metastases via Dual-Isocenter VMAT Stereotactic Radiosurgery, Medical Dosimetry, 46 240-246. 7 pages, dated Jan. 8, 2021.
International Searching Authority, International Search Report and Written Opinion issued in Application No. PCT/EP2022/087266, 12 pages, dated Jul. 14, 2023.
Pokhrel, Damodar, et al., Dynamic conformal arcs-based single-isocenter VMAT planning technique for radiosurgery of multiple brain metastases, Medical Dosimetry, 46 195-200, 6 pages, dated Nov. 18, 2020.

* cited by examiner

COMPUTER-IMPLEMENTED MEDICAL METHOD FOR RADIATION TREATMENT (RT) PLANNING FOR TREATING MULTIPLE LESIONS OF A PATIENT

FIELD OF THE INVENTION

The present invention relates to a computer-implemented method for radiation treatment (RT) planning for treating multiple lesions of a patient, a corresponding computer program, a non-transitory program storage medium storing such a program, as well as a medical system.

TECHNICAL BACKGROUND

For radiation treatment planning in the field of radiotherapy and/or radiosurgery, very sophisticated software programs are applied in order to find an appropriate or even the best radiation plan for the given medical and technical circumstances. In particular, such state of the art radiation treatment planning software solutions allow the medical practitioner to provide details about the following considerations to the software system.

Typically, a planning target volume associated with or representing e.g. a lesion (referred to herein also as target) or metastasis is specified along with a desired prescribed dose. The prescribed dose should preferably be deposited in at least a partial volume, also referred to as coverage volume, of the planning target volume in order to ensure biological effectiveness of the irradiation treatment. Apart from that, one or more constraints to be fulfilled during irradiation treatment can be specified. Typically, an organ at risk like e.g. an eye of the patient, which preferably is to be spared during irradiation treatment or which should not receive more than an allowed dose in at least a partial volume thereof, can be specified as constraint. An optimization is carried out, which considers the specified planning target volume, a desired dose value defined by the radiologist, the one or more constraints, usually the coverage volume of the planning target volume is determined and a corresponding irradiation treatment plan is generated. This is done by an optimization algorithm, a so-called optimizer, in the software that is available since years. The irradiation treatment plan can then be utilized to carry out the actual irradiation treatment.

However, particularly for multiple brain metastases treatment planning the difficulty arises how to define the arc setup, which is then used by the gantry of the radiation treatment apparatus to carry out the irradiation of the patient. Such an arc setup comprises a plurality of arcs, each arc being defined by a combination of a patient table angle, a gantry start angle and a gantry stop angle. In other words, an arc setup defines a set of arc trajectories, wherein each trajectory is defined by a gantry start and gantry stop angle and a unique table angle. Prior art solutions of the Brainlab AG are described in e.g., the documents WO 2015/039903 A1 and WO 2013/075743 A1.

One available software solution of Brainlab AG called "Multiple Brain Mets SRS" software is a treatment planning software that produces treatment plans consisting of dynamic conformal arcs (a treatment modality for linac-based radiation therapy in which the linac head rotates around a patient, utilizing a gantry) with a single iso-center as described in WO 2013/075743 A1. The software has a high degree of automation, to allow for optimization of arc geometry and conformal shapes. Fields are collimated dynamically using a multi-leaf collimator while the gantry of the linac rotates around the patient's head. The fields are shaped according to projections of the metastases for a finite set of gantry angles (control points). For each control point, a projected shape can be either opened or blocked to alter the dose contribution. Moreover, a negative or positive 2D margin can be added to the projected shape to influence the dose profile. Finally, monitor units (arc-weights) must be set per arc (single rotation of the gantry). Monitor units are a measure of linac output and influence treatment time and efficiency.

Moreover, Brainlab's Cranial SRS provides software to generate modulated treatment plans for single targets using volumetric intensity modulated arc therapy (VMAT). As is understood by the skilled reader, using VMAT means using modulated apertures of the collimator, and thus, the apertures are independent of the target's projection. The software has a high degree of automation, allowing for optimization of arc geometry and modulated shapes.

Some customers may create manual hybrid treatment plans by planning a subset of targets using Multiple Brain Mets SRS and (a) specific target(s) using Cranial SRS subsequently. This is rather cumbersome as the total plan cannot be conveniently reviewed and managed at once. Also, adding the two (or more) plans might result in over- and/or under-dose which was never observed by the optimization algorithm. Also, Multiple Brain Mets SRS 4.0 provides a first version of hybrid planning. The beforementioned manual approach is automized. The subsequent VMAT optimization is performed in the same application, taking into consideration the dose of the conformal arcs during VMAT optimization.

However, the inventors of the present invention have identified that the prior art approaches have some limitations. For example, only one target can be treated using VMAT arcs. Also, the method works sequentially. In particular, VMAT arcs will always add dose to the targets treated only with conformal arcs and normalization of some of the arcs does not always work well.

The inventors have also recognized that when using conformal apertures or conformal arcs for large targets, targets close to risk structure, targets close to one or more surfaces, targets close to air, tissue and/or bone interfaces, non-spherical targets, and very homogeneous dose prescriptions, the conformity of the dose distribution may be undesirable. In other words, the desired dose distribution regarding e.g. target conformity or the sparing of non-target tissue cannot be achieved. Moreover, when using VMAT/modulate apertures and/or arcs, although highly modulated arcs may yield very complex dose distributions, dose calculation and delivery accuracy may be problematic, especially for small targets and/or targets, which are further away from isocentre.

It is, therefore, desirable to provide for an improved radiation treatment planning for treating multiple lesions of a patient, e.g., allowing to advantageously combine one or more benefits of VMAT (modulated) apertures and/or arcs with one more benefits of using conformal apertures and/or arcs. This is achieved with the present invention as will be explained in more detail hereinafter.

The present invention can be used for radiotherapy or radiosurgery procedures, such as the cranial/spine stereotactic radiosurgery treatment planning system, e.g. in connection with ExacTrac®, which is a product of Brainlab AG.

Aspects of the present invention, embodiments, examples and exemplary steps are disclosed in the following. Different embodiments, examples and exemplary features of the invention can be combined in accordance with the invention wherever technically expedient and feasible.

EXEMPLARY SHORT DESCRIPTION OF THE INVENTION

The present invention overcomes some or all of said limitations of the prior art.

In particular, the present invention provides a beneficial way of calculating an RT treatment plan, which combines conformal and modulated apertures or beams for multiple targets like lesions or metastases of a patient in one RT treatment plan.

For example, the presented method, program and system have no inherit limitation on the number of lesions, i.e., targets, treated with VMAT apertures and/or VMAT arcs. Moreover, the dose distribution for all lesions, i.e., targets, can be optimized at the same time. Preferably, at each iteration of the optimization algorithm suggested herein, the dose for all lesions is known. This will be explained in more detail hereinafter, especially in the context of particular exemplary embodiments.

A gist of the invention may be seen in initializing the VMAT problem with a conformal arc plan, as will be explained in detail hereinafter. The present invention can beneficially use all existing technology for packing, arc setup optimization, and/or iso-dose line prescription optimization. Further, the VMAT optimizer disclosed herein and used in the presented method may use the initialized apertures and/or arcs to further optimize conformity and iso-dose line prescription of all lesions at the same time. In addition, it may also further optimize the normal tissue dose and/or dose to risk structures.

As will become apparent from the present disclosure, the present invention defines a novel approach to automatically find an optimized RT plan for a particular patient having a plurality of lesions or metastasis. The presented method advantageously uses a VMAT optimization, which allows for a conformal and a modulated optimization.

The skilled reader will appreciate that within the presented method a manual or computer implemented decision is made for one or more lesions of the patient, whether conformal or modulated apertures/arcs/beams shall be used for said lesion. This decision or determination may be made for one, for more or even all spatial angles from which the irradiation can be emitted by the RT apparatus used. Further, a DCA optimization is carried out, which provides a first treatment plan. This DCA optimization can be carried out for one, for more, or preferably for all lesions of said patient. Further, a VMAT optimizer is initialized with said first treatment plan that the DCA optimizer delivers. Moreover, the so initialized VMAT optimizer runs a DCA optimization for those apertures, arcs, and/or metastasis, which were found to be applied or irradiated in a conformal manner. And the VMAT optimizer runs a VMAT optimization for the remaining apertures, arcs and/or metastasis.

Note that in the context of the present invention, the beneficial combination of modulated irradiation and conformal irradiation can be realized on different levels. It will thus be explained in detail hereinafter that during the step S1 of the presented method it is determined or decided for at least one lesion of the patient, which apertures of the Multi Leaf Collimator (MLC) of the radiation treatment (RT) apparatus shall be used in a conformal manner. This determination may result in one exemplary embodiment in an extreme outcome that only one conformal aperture shall be used, i.e., to be used during irradiation from one particular spatial angle, whereas the remaining apertures of the radiation treatment plan shall be used in a modulated manner. Moreover, in another exemplary embodiment all apertures of one or more particular arcs are determined in step S1 to be used in a conformal manner, whereas the apertures of the remaining arcs of the radiation treatment plan shall be used in a modulated manner. Further, in another exemplary embodiment the determination of step S1 results in the outcome that one or more particular lesions of the patient are to be irradiated entirely with only conformal arcs. In other words, said lesions shall be irradiated from all spatial angles with only conformal apertures, and hence all arcs used for said one or more lesions only use conformal apertures. In the context of this embodiment, the remaining lesions of the patient may be irradiated with only modulated apertures or with a combination of conformal and modulated apertures. Therefore, the presented method makes use of the possibility to have conformal apertures from some directions and modulated apertures from some other directions. All combinations of conformal and modulated apertures for irradiating a plurality of lesions are thus covered. This will be further elucidated hereinafter in the context of particular embodiments.

It should be noted that the present invention can of course be applied not only to multiple brain metastases, but to any other multiple targets within a human body.

In the following, a short description of the specific features of the present invention is given which shall not be understood to limit the invention only to the features or a combination of the features described in this section.

GENERAL DESCRIPTION OF THE INVENTION

In the following section, a description of the general features of the present invention is given, for example by referring to possible embodiments of the invention.

As stated above, it may be desirable to provide for an RT planning method allowing to advantageously combine benefits of VMAT (modulated) apertures with benefits of using conformal apertures for multiple brain target treatment planning of an individual patient.

This is achieved by the subject-matter of the independent claims, wherein further embodiments are incorporated in the dependent claims and the following description.

According to a first aspect of the present invention a computer-implemented medical method for radiation treatment (RT) planning for treating multiple lesions of a patient is presented. The method comprises the steps of:

determining for at least one lesion of the patient, preferably for all lesions of the patient, one or more conformal apertures to be used during radiation treatment (step S1);

performing a treatment plan optimization based on conformal shapes for one or more, preferably all, lesions of the patient using a dynamic conformal arc (DCA) optimizer thereby calculating a first irradiation treatment plan (step S2);

using the calculated first irradiation treatment plan as initialisation of a volumetric intensity modulated arc therapy (VMAT) optimizer (step S3);

performing an optimization for all lesions of the patient using the initialized VMAT optimizer (step S4), and wherein the VMAT optimizer keeps all conformal apertures, which were determined in step S1, conformal during performing the optimization in step S4.

As is understood be the skilled reader, the method presented herein provides a hybrid RT plan, which contains a combination of one or more conformal apertures with one or more modulated apertures. As an exemplary MLC field for a hybrid treatment plan generated according to the present invention, FIG. 3, which will be described herein below, shows two lesions that according to the present invention will be irradiated with an RT plan that beneficially combines modulated and conformal arcs. The aperture for the small, rather spherical lesion shown in FIG. 3 has a conformal shape. And the larger, less spherical lesion has multiple smaller apertures. The respective shape is modulated when carrying out the underlying RT plan calculated when following the present invention. In this way, the presented method makes use of the strength of the DCA optimization, which advantageously solves the normalization problem and at the same time makes use of the strength of the VMAT optimization, which advantageously solves the problem of organ at risks. In general, VMAT can be used for higher control over the shape of the dose distribution.

The subset of lesions/arcs which are irradiated using conformal fields could be automated or manually set by a user. The automation could for instance be based on data analysis of customer data or simulations.

The existing VMAT optimizer allows modulated apertures, i.e., modulated fields, by definition. As part of this invention and as described herein, some apertures or shapes shall be restricted to achieve conformal fields. This is ensured by the VMAT optimizer, which keeps all conformal apertures, which were determined in step S1, conformal during performing the optimization in step S4. Thus, the VMAT optimizer has this particular restriction and/or particular configuration that those apertures, which are determined in step S1 to be applied as conformal apertures, must stay conformal during the optimization run by the VMAT optimizer. As is clear to the skilled reader, these fields may still have beam's-eye-view margins as described in the patent EP 3497702 B1 of the Brainlab AG.

In other words, the VMAT optimizer suggested herein is configured for performing a DCA optimization for those apertures, which were determined to be conformal. And the VMAT optimizer is configured for performing a VMAT optimization for the apertures of the patient, for which an irradiation with modulated arcs is determined.

Conformal arc optimization, i.e., closing and opening certain apertures, changing beam's-eye-view-margins, and/or changing arc weights, may be simplified with the present invention to reduce the computation time. An example is using coarser dose grid resolutions.

To yield an efficient RT plan, i.e., a minimal number of table angles and monitor units, the parameters for arc setup optimization can be optimized. In particular, the proposed required minimum and maximum number of table angles is expected to be less for VMAT arcs than for conformal arcs. The packing algorithm may also need a different parametrization. During packing, leaf pairs which treat multiple targets for a single field may be allowed, as the VMAT optimization algorithm may compensate the potentially unnecessary normal tissue dose by e.g., moving the leaves of the MLC or changing the beam weight corresponding to the field. This will be explained in more detail hereinafter.

Regarding the step S1, in which the conformal apertures are determined, the following should be noted. In a first exemplary outcome, for said decision whether conformal or modulated apertures/arcs shall be used, the outcome is that for one or more lesions one conformal aperture shall be used from one spatial angle. In a second, exemplary outcome, for one or more lesions, one or more entire arcs shall use conformal apertures. And in a third, exemplary outcome one or more lesions shall be irradiated always and from any spatial angle, i.e., with each arc, in a conformal manner. In such a case, the outcome would be that particular lesions are to be irradiated conformally, irrespective of the spatial angle and hence only conformal apertures would be used for said one or more lesions. Different combinations thereof are of course possible and covered by the method presented herein. For example, for a patient having e.g., five lesions and applying the suggested method, two lesions could be classified as "conformal lesions", defining that these lesions would definitely have to be irradiated only with conformal apertures. Two other lesions could be classified as "VMAT/modulated" lesions, where only modulated apertures would be applied. In this non-limiting example, the remaining fifth lesion could be classified as a lesion where some apertures of some arcs shall be conformal, whereas the remaining apertures shall be modulated.

Thus, the presented method can could be applied by enforcing conformal fields on the aperture level, or for a segment of an arc, or for the whole arc, or for the whole lesion. But mechanical constraints, like e.g., leaf speed of the MLC can be considered as well.

Note that it is sufficient for the determination of step S1 if only the apertures are determined, which shall be used in a conformal manner. Thus, the conformal apertures are selected/chosen. The remaining apertures are thus automatically considered to be applied in a modulated manner. Determining the conformal apertures thus automatically also determines the modulated apertures. The apertures to be used in an RT plan suggested herein are either conformal or modulated. In the same way it is sufficient for realizing this feature if only the modulated apertures are determined, since the remaining apertures are automatically considered to be conformal apertures.

In case a user wants to apply step S1 of the presented method for a) all apertures of one arc, or even for b) all apertures of all arcs of one lesion, this is covered by the presented method as well. In case a), it is determined in step S1, which arcs shall use only conformal apertures. In case b), it is determined in step S1, which lesions shall entirely be irradiated only with conformal apertures, i.e., shall be irradiated from each spatial angel and hence by each arc with conformal apertures.

The determination or decision in step S1 may be carried out by receiving a user input or by acquiring data from a user thereabout. For said determine/decision the following insights may be considered. For conformal apertures and conformal arcs, the conformity of the dose distribution may be undesirable for large targets, targets close to risk structure, targets close to a surface, targets close to air, targets close to tissue and/or targets close to bone interfaces, non-spherical targets, and very homogeneous dose prescriptions. In step S1, it may thus be considered for such targets/lesions that not conformal apertures or arcs are preferred, but modulated apertures or arcs. Moreover, for modulated/VMAT apertures and arcs it should be considered that although highly modulated arcs may yield very complex dose distributions, dose calculation and delivery accuracy may be problematic, especially for small targets and/or targets further from iso-center. Thus, in such cases it should be considered during step S1 that not a modulated aperture/arc is preferred, but a conformal aperture/arcs. Beneficially, the presented method takes this into account.

Note that in step S2, in which a treatment plan optimization is run based on conformal shapes for one or more lesions, the optimization algorithm in S2 may only generate apertures with conformal shapes. Further, said conformal shapes are the shapes of the apertures that were defined or determined in step S1. In other words, in step S2 a conformal shape optimization is performed for one or more or all lesions of the patient using a dynamic conformal arc (DCA) optimizer.

Typically, not all lesions or metastasis are treated in a single treatment plan, e.g., because a doctor rather awaits its progress. Therefore, the present invention of course also applies to applications where a patient may have e.g., five lesions, but the method presented herein is only applied for e.g., two, three of four lesions thereof. The lesions treated in such an RT treatment may thus be considered as target volumes.

Moreover, in step S2 a first treatment plan is calculated. This covers not only the calculation of a final treatment plan that can be readily applied by an RT apparatus, but also covers the calculation of an approximation of a treatment plan only. In that sense, calculating a first treatment plan, which is not deliverable by an RT apparatus, i.e., a treatment machine, or calculating a first treatment plan where one does not calculate the dose properly, is covered by step S2 as well.

As is understood by the skilled reader, the method presented herein may determine, which lesions or arcs need modulation, and which not. In an optional step an arc setup optimization is performed, as will be explained in more detail hereinbelow. Further, a conformal shape optimization is performed, preferably for all targets. Moreover, a VMAT optimization is performed with conformal shapes for a subset of lesions/arcs.

According to an exemplary embodiment of the present invention, the benefits of conformal arcs and modulated arc are combined by generation of treatment plans using hybrid arcs. This method allows that each arc can contain both conformal and modulated apertures.

According to an exemplary embodiment of the present invention, the determination of step S1 is carried out for at least one irradiation angle, preferably for all irradiation angles, facilitated by a radiation treatment (RT) apparatus, and wherein an irradiation angle is defined by a combination of a patient table angle and a gantry angle.

This embodiment details that the determination regarding the conformal and/or modulated apertures or arcs can be carried out irradiation angle per irradiation angle. An exemplary RT apparatus is shown in FIG. 2 and explained in the corresponding description. Also, a definition is provided for the term irradiation angle. This is the definition know to the skilled reader, as is confirmed by the patent EP 3817809 B1 of the Brainlab AG.

According to an exemplary embodiment of the present invention, wherein the determination of step S1 is dependent from at least one of a shape of the respective lesion of the patient, an organ at risk (OAR) of the patient, a previous result of this determination of step 1 for another irradiation angle, wherein an irradiation angle is defined by a combination of a patient table angle and a gantry angle, one or more mechanical constraints, for example, of a Multi Leaf Collimator (MLC) of a radiation treatment (RT) apparatus, or of an irradiation source of the radiation treatment (RT) apparatus, proximity of other lesions, size of the respective lesion, and location of the respective lesion in a body of the patient.

This embodiment specifies particular parameters for which the inventors found that they have a significant influence on the selection of the lesions or metastases that are to be irradiated with conformal arcs/modulated arcs. Considering one or more of these parameters increases the precision, with which the patient can be treated with the resulting RT plan. Thus, for the determination of the conformal/modulated apertures, arcs or lesions, at least one of these parameters shall be taken into account.

According to an exemplary embodiment of the present invention, the method comprises the step providing the VMAT optimizer with a dose prescription for said patient, wherein the dose prescription defines prescribed dose values to be delivered to one or more of the lesions of the patient, and/or one or more dose limits for organs at risk/risk structures of the patient.

According to this embodiment, the VMAT optimizer not only is provided with the result of the DCA optimizer provided in step S2 and with the restrictions about the one or more apertures/lesions that are to be irradiated in a conformal way, but that it also gets as input the radiological prescription. Thus, the initialized VMAT optimizer takes into account the prescribed dose values to be delivered, and/or one or more dose limits for organs at risk/risk structures of the patient when performing the optimization for all lesions of the patient in step S4. This will increase the accuracy and precision of the RT treatment of the patient when using the correspondingly created or calculated RT treatment plan.

According to an exemplary embodiment of the present invention, the determination of step 1 is carried out by receiving a user input about the at least one lesion of the patient, preferably about all lesions of the patient, and about information whether the at least one lesion is to be irradiated with conformal apertures or with modulated apertures.

The user may provide the corresponding data via a computer and/or a user interface such that the corresponding algorithm can use said data for calculating the respective RT treatment plan. For example, the user, e.g., a radiation therapist, brain surgeon or a radiologist, may input data into the computer carrying out the presented method, which data describe or define which apertures shall be conformal and which shall ne modulated. In other words, said data provided by the user may define from which spatial angle or direction conformal apertures shall be used and from which spatial angle or direction modulated apertures shall be used. In a particular embodiment, said data provided by the user may define which lesion of the patient shall be purely irradiated in a conformal manner, and/or which lesion of the patient shall be purely irradiated in a modulated manner.

According to another exemplary embodiment of the present invention, the determination of step 1 is done automatically by a software. In this embodiment the determination of step 1 is carried by a computer-implemented method of automatically determining for the at least one lesion of the patient, preferably for all lesions of the patient, one or more conformal apertures to be used during radiation treatment. In a preferred embodiment, said automatic determination is based on data analysis of customer data, and/or is based on a simulation.

According to an exemplary embodiment of the present invention, the determination of step 1 is carried out before the optimization for all lesions of the patient using the VMAT optimizer is carried out in step S4, or the determination of step 1 is carried out during the optimization for all lesions of the patient using the VMAT optimizer in step S4.

This embodiment relates to the case or scenario where the determination of step S1 about conformal/modulated apertures/arcs is carried out before the VMAT optimization is carried out, i.e., as a separate step from which the results can be used during the VMAT optimization. Alternatively, step S1 is carried out while the VMAT optimization is performed.

In that sense, the VMAT optimizer may be trained while the optimization is running as to which apertures shall be conformal and which shall be modulated. This can e.g. be achieved by looking at the dosimetric consequences of using conformal or modulated shapes and having a threshold that snaps the VMAT optimizer into only using a conformal shape for a certain gantry direction if the benefits of a modulated aperture are marginal. In other words, the "algorithm" for automatically determining if conformal/modulated apertures shall be used can either be executed before the VMAT optimizer is called (thus, the decision is an input for the VMAT optimizer), or the "algorithm" can be executed "within" the VMAT optimizer. Conceptually, this may be seen and similar or identical, but it is a matter of where it is implemented. Moreover, one may see this as an implementation in which the VMAT optimizer "finds out dosimetrically" what lesions benefit from one or more conformal fields. E.g. the optimizer could try both modulation/conformal for some shapes and only pick modulated if it actually improves the dose distribution by some metric. In this case it has to be within the optimizer.

According to another exemplary embodiment of the present invention, during the step S4 of optimization using the VMAT optimizer a second irradiation treatment plan is calculated.

It is defined in this embodiment that during or after the VMAT optimization the second, i.e., final treatment plan is generated. This calculated irradiation treatment plan may then be provided to the RT apparatus, as e.g., depicted in FIG. 2 for treating the patient. The second treatment plan may be sent to the device automatically or may be stored for review by a radiation therapist, a radiologist or another user.

According to another exemplary embodiment of the present invention, the calculated second irradiation treatment plan uses at least one hybrid arc containing both conformal apertures of a Multi Leaf Collimator (MLC) of a radiation treatment (RT) apparatus and modulated apertures of the MLC of the RT apparatus.

In this embodiment it is made explicit clear that in the second treatment plan generated with the method presented herein, at least one hybrid arc, which contains modulated apertures and conformal apertures is comprised. In one example, the method may generate an RT plan which purely consists of hybrid arcs, however, in another embodiment only a part of all arcs are hybrid arcs, whereas the remaining non-hybrid arcs are either conformal arcs, i.e., arcs that only use conformal apertures, or modulated arcs, i.e., arcs that only use modulated apertures, or a mixture of conformal arcs and modulated arcs. The two-step optimization carried out in steps S1 to S4 as disclosed herein will calculate the best possible outcome regarding the use of hybrid arcs.

According to another embodiment of the present invention, during the optimization of step S4 using the VMAT optimizer a respective dose distribution for all lesions of the patient is optimized at the same time.

During the VMAT optimization all targets are optimized together, which is one of the key benefits of the present invention over the sequential hybrid solution that is known in the prior art. As was mentioned before, the VMAT optimizer is configured for carrying out a DCA optimization for said apertures, which were determined in step S1 to be conformal, and carries out a VMAT optimization for the remaining apertures.

According to another exemplary embodiment of the present invention, at each iteration of the optimization of step S4 using the VMAT optimizer the respective dose for each lesion of the patient is known.

This embodiment specifies that since the VMAT is initialized with the DCA plan and sine the VMAT optimizer optimizes all target volumes, i.e., all the lesions that are used for applying the present invention, together the algorithm/the user always knows the respective dose for each lesion. In other words, at each iteration of the optimization of step S4 using the VMAT optimizer the dose for all lesions of the patient is known. This provides a benefit over the prior art, where the dose is only known at the end of the optimization. In contrast thereto, with the method of the present invention at each iteration of the optimization algorithm the dose for all lesions is known.

According to another exemplary embodiment of the present invention, the initialisation of the VMAT optimizer in step S3 contains a provision of initialized apertures based on the calculated first irradiation treatment plan. And the method comprises the step using, by the VMAT optimizer and during the optimization step S4, the initialized apertures for further optimizing at least one of conformity, iso-dose line prescription of all lesions at the same time, normal tissue dose and dose to risk structures, gradient index, treatment time, and modulation complexity.

In a particular embodiment thereof, the DCA plan created in step S2 defines arcs, which are then used by the VMAT optimizer as "initialized arcs". Thus, the initialization of the VMAT optimizer is not or not only applied on the aperture level, but on the arc level. Using a combination of one or more apertures with one or more arcs for initializing the VMAT optimizer is thus part of an embodiment of the present invention.

According to another exemplary embodiment of the present invention, the method comprises the step of performing an arc setup optimization. Preferably, such an arc set up optimization can be carried out as disclosed in detail in the patent EP 3817809 B1 of the Brainlab AG.

Preferably, said arc set up optimization comprises:
acquiring a first arc setup comprising a plurality of arcs, each arc being defined by a combination of a patient table angle, a gantry start angle and a gantry stop angle,
distributing a plurality of target volumes, which describe the lesions of the patient, to the arcs of the first arc setup thereby providing a packed first arc setup,
comparing said first packed arc setup with one or more predefined arc setup constraints,
wherein the one or more predefined arc setup constraints are selected from: the number of patient table angles per target volume, the number of passes, the sum of gantry span per metastasis over all arcs, the minimum table span, and the total number of patient table angles, and the method comprising the step of
automatically suggesting at least a second arc setup based on a result of the comparison; and
using the suggested second arc setup during performing the treatment plan optimization based on conformal shapes using the DCA optimizer in step S2 as described herein.

In a further preferred embodiment relating to the arc setup optimization, for each of the one or more predefined arc setup constraints a minimum and a maximum is defined. In a further preferred embodiment, the predefined arc setup constraint about the number of patient table angles defines a minimum number of patient table angles,
wherein, if a result of the comparison of the first packed arc setup with the one or more predefined arc setup constraints is that the minimum of the number of patient table angles is not violated, the method comprises the step removing a patient table angle from the first arc setup; and/or wherein the predefined arc setup constraint about the number of passes defines a minimum number of passes, wherein, if the result of the comparison of the first packed arc setup with the one or more predefined arc setup constraints is that the minimum of the number of passes is not violated, the method comprises the step removing a pass from the first arc setup.

According to a second aspect of the present invention, a program which, when running on a computer or when loaded onto a computer, causes the computer to perform the method steps of any of the methods disclosed herein.

Thus, in this second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, for example the internet. The invention according to the second aspect therefore, may alternatively or additionally relate to a data stream representative of the aforementioned program.

Several iterations of such a method can be carried out based on e.g., the comparison between an arc setup and the following, subsequent arc setup in the iteration. If this optimization is converging, which can be controlled by means of e.g., a predefined convergence criterion, this method of automatically finding an optimized arc setup may be stopped and the result may be further used in completely defining the radiotherapy treatment plan.

It should be notated that the presented method may be repeated in several iterations. Thus, the different embodiments explained herein after in detail may also be applied during such iterative repetitions of the presented method. In other words, the presented method can be repeated until a desired "quality" or grade of the finally suggested arc setup, i.e., the arc setup suggested by the presented method in the last iteration, is achieved.

In a third aspect, the invention is directed to a non-transitory computer-readable program storage medium on which the program according to the second aspect is stored.

In a fourth aspect, the invention is directed to a medical system comprising:

a) at least one computer;

b) at least one electronic data storage device storing at least patient data describing the multiple lesions of the patient; and c) a medical device for carrying out a medical procedure on the patient, wherein the at least one computer is operably coupled to the at least one electronic data storage device for acquiring, from the at least one data storage device, the patient data describing the multiple lesions of the patient, and the medical device for issuing a control signal to the medical device for controlling the operation of the medical device on the basis of a result of the optimization carried out in step 4 according to any of the methods disclosed herein.

In an embodiment of the medical system, the medical device comprises a radiation treatment (RT) apparatus comprising a treatment beam source and a patient support unit. The at least one computer is operably coupled to the radiation treatment apparatus for issuing a control signal to the radiation treatment apparatus for controlling, on the basis of a result of the optimization carried out in step 4 according to any of the methods presented herein, at least one of the operation of the treatment beam source or the position of the patient support unit.

An exemplary system is a radiotherapy or radiosurgery system, e.g. ExacTrac.

Note that the invention does not involve or in particular comprise or encompass an invasive step, which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to optimizing an arc setup. For this reason alone, no surgical or therapeutic activity and in particular, no surgical or therapeutic step is necessitated or implied by carrying out the invention.

Definitions

In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression acquiring data like e.g. an arc setup for example encompasses (within the framework of a computer implemented method) the scenario in which the arc setup is determined by the computer implemented method or program. Determining data, i.e. an arc setup, for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Treatment Beam

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_vmat.php and http://www.varian.com/us/oncology/treatments/treatment_techniques/rapidarc.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

In the following, a short description of the specific features of the present invention is given which shall not be understood to limit the invention only to the features or a combination of the features described in this section.

Figure 1:
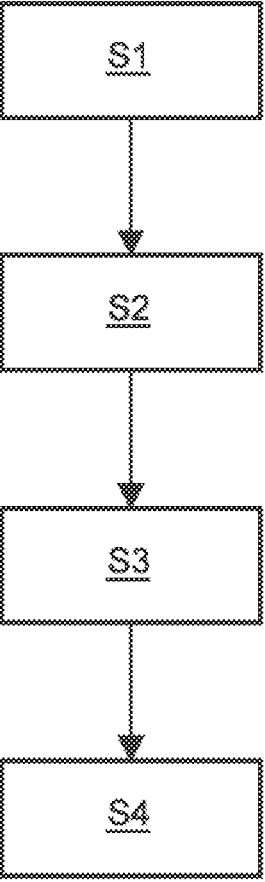
FIG. 1 illustrates a flow diagram of a computer-implemented medical method for radiation treatment (RT) planning for treating multiple lesions of a patient according to an exemplary embodiment of the present invention.

FIG. 1 shows a computer-implemented medical method for radiation treatment (RT) planning for treating multiple lesions of a patient. For example, for a patient having e.g., five lesions and applying the suggested method, two lesions could be classified as "conformal lesions", defining that these lesions would definitely have to be irradiated only with conformal apertures. Two other lesions could be classified as "VMAT/modulated" lesions, where only modulated apertures would be applied. In this non-limiting example, the remaining fifth lesion could be classified as a lesion where some apertures of some arcs shall be conformal, whereas the remaining apertures shall be modulated. This will be detailed now.

The method of FIG. 1 comprises the following steps. In step S1 it is determined for at least one lesion, i.e., a target volume, of the patient, preferably for all lesions of the patient, one or more conformal apertures to be used during radiation treatment. In step S2, a treatment plan optimization is carried out based on conformal shapes for one or more, preferably all, lesions of the patient using a dynamic conformal arc (DCA) optimizer thereby calculating a first irradiation treatment plan. Note that this covers not only the calculation of a final treatment plan that can be readily applied by an RT apparatus as the one shown in FIG. 2, but also covers the calculation of an approximation of a treatment plan only. The method also comprises the step of using the calculated first irradiation treatment plan as initialisation of a volumetric intensity modulated arc therapy (VMAT) optimizer, i.e., step S3. Further, the so initialized VMAT optimizer is run, and it performs an optimization for all lesions of the patient in step S4. Note that the VMAT optimizer is restricted and/or configured to keep all conformal apertures and/or all conformal arcs, which were determined in step S1 to be conformal, conformal also during the optimization that is carried out or performed in step S4. Thus, the VMAT optimizer carries out a DCA optimization for said apertures, which were determined to be conformal, and carries out a VMAT optimization for the remaining apertures.

Therefore, the method shown in FIG. 1 beneficially combines the benefits of conformal apertures/arcs and modulated apertures/arc by generation of treatment plans using conformal and modulated apertures. Also, hybrid arcs may be used, and in a particular embodiment thereof each arc contains both conformal and modulated apertures. In this way, the presented method makes use of the strength of the DCA optimization, which advantageously solves the normalization problem and at the same time makes use of the strength of the VMAT optimization, which advantageously solves the problem of organ at risks. In general, VMAT can be used for higher control over the shape of the dose distribution. The presented method advantageously uses a VMAT optimization, which allows for a conformal and a modulated optimization.

The determination or decision in step S1 may be carried out by receiving a user input or by acquiring data from a user thereabout. For said determine/decision the following insights may be considered. For conformal apertures and conformal arcs, the conformity of the dose distribution may be undesirable for large targets, targets close to risk structure, targets close to a surface, targets close to air, targets close to tissue and/or targets close to bone interfaces, non-spherical targets, and very homogeneous dose prescriptions. In step S1, it may thus be considered for such targets/lesions that not conformal apertures or arcs are preferred, but modulated apertures or arcs. Moreover, for modulated/VMAT apertures and arcs it should be considered that although highly modulated arcs may yield very complex dose distributions, dose calculation and delivery accuracy may be problematic, especially for small targets and/or targets further from iso-center. Thus, in such cases it should be considered during step S1 that not a modulated aperture/arc is preferred, but a conformal aperture/arcs. Beneficially, the presented method takes this into account.

Positively, the method suggested herein also facilitates the use of existing technology that can be combined with the present invention. It may be seen as a gist of the invention to initialize the VMAT problem with a conformal arc plan, as was explained hereinbefore in detail. In a particular embodiment, the suggested method may also use the known technology for packing, as e.g., suggested in the EP2782642 B1 of the Brainlab AG, the known technology for arc setup optimization, as suggested by the patent EP3817809 B1 of the Brainlab AG, and the known technology for isodose-line prescription optimization, as suggested in the patent EP3497702 B1 of the Brainlab AG. The VMAT optimizer suggested in the present disclosure can advantageously use the initialized apertures and/or arcs to further optimize conformity and iso-dose line prescription of all targets at the same time, as well as normal tissue dose and dose to risk structures.

Figure 2:
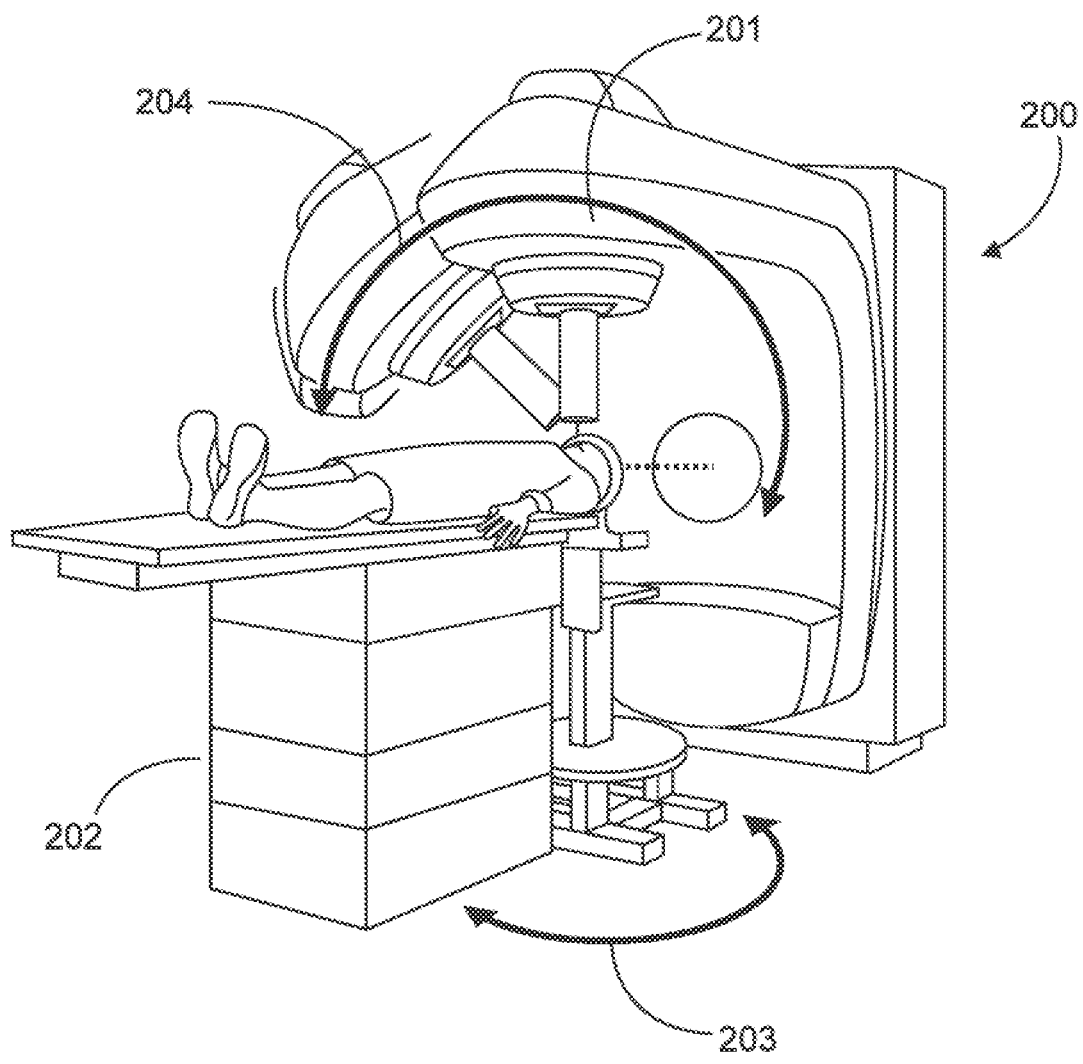
FIG. 2 schematically shows a radiation treatment (RT) apparatus according to an exemplary embodiment of the present invention.

FIG. 2 schematically shows a radiation treatment (RT) apparatus 200 according to an exemplary embodiment of the present invention. The RT apparatus 200 comprises a treatment beam source 201 and a patient support unit 202, which is embodied as a patient table 202. At least one computer is operably coupled to the RT apparatus for issuing a control signal to the radiation treatment apparatus for controlling the operation of the treatment beam source 201 and/or the position of the patient support unit 202. The controlling of the treatment beam source 201 and/or the position of the patient support unit 202 can be based on the basis of a result of the optimization carried out in step 4 according to any of the methods described herein, e.g., the method shown in FIG. 1. In FIG. 2 the patient table angle is depicted by arrow 203 and the gantry angle is depicted by arrow 204.

An RT plan to be used by the RT apparatus 200 shown in FIG. 2 and being calculated or generated using an embodiment of the present invention may be provided as follows. First, at least one lesion of the patient, but preferably for all lesions of the patient (which are selected to be treated with the present invention), it is determined whether it is to be Irradiated with conformal apertures/arcs or with modulated arcs/apertures. Second, conformal shape optimization is performed for some or all lesions of the patient using a dynamic conformal arc (DCA) optimizer thereby calculating a first irradiation treatment plan. Third, the calculated first irradiation treatment plan is used for initializing a volumetric intensity modulated arc therapy (VMAT) optimizer. The so initialized VMAT optimizer caries out an optimization for all selected lesions of the patient using the so initialized VMAT optimizer. Moreover, the VMAT optimizer performs a DCA optimization for all lesions of the patient, for which an irradiation with conformal apertures/arcs is determined in the first step. Further, the VMAT optimizer performs a VMAT optimization for all lesions of the patient, for which it is not determined in the first step that conformal arcs are to be used. Thus, the beneficial combination of conformal and modulated beams for multiple targets, as suggested herein, is provided to the user. The RT apparatus 200 shown in FIG. 2 may then use this RT plan to apply an improved RT treatment of the patient.

Figure 3:
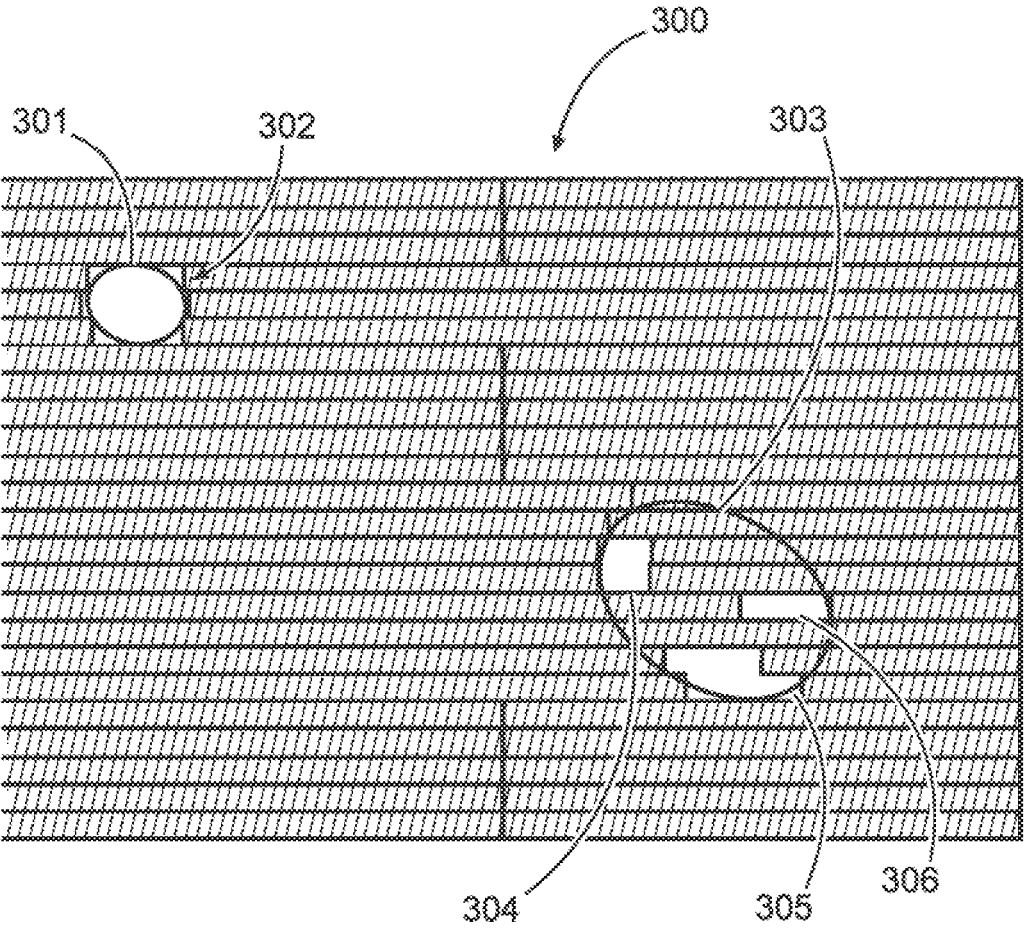
FIG. 3 schematically shows an MLC of a radiation treatment (RT) apparatus using a RT treatment plan generated with a method according to an exemplary embodiment of the present invention.

FIG. 3 schematically shows a multileaf collimator or multiple leaf collimator (MLC) 300. MLC 300 is a collimator or beam-limiting device that is made of individual "leaves" of a high atomic numbered material, usually tungsten, that can move independently in and out of the path of a radiotherapy beam in order to shape it and vary its intensity. MLCs are used in external beam radiotherapy to provide conformal and modulated shaping of RT beams. Specifically, conformal radiotherapy and VMAT treatment plans can be delivered using MLCs. As is understood be the skilled reader, the method presented herein provides a hybrid RT plan, which contains a combination one or more conformal apertures with one or more modulated apertures. As an exemplary MLC field for a hybrid treatment plan generated according to the present invention, FIG. 3 shows two lesions 301 and 303, which according to the present invention are irradiated with an RT plan that beneficially combines modulated apertures 304 to 306 and a conformal aperture 302. The aperture for the small, rather spherical lesion 301 shown in FIG. 3 has a conformal shape. And the larger, less spherical lesion 303 has multiple smaller apertures 304 to 306. The respective shape is modulated when carrying out the underlying RT plan calculated when following the present invention, e.g., the method described in the context of FIG. 1. The presented method advantageously uses a VMAT optimization, which allows for a conformal and a modulated optimization.

The invention claimed is:

1. A computer-implemented method for radiation treatment (RT) for treating multiple lesions of a patient, the method comprising:

determining for at least one or more lesions of the patient, one or more conformal apertures to be used during radiation treatment;

performing a treatment optimization based on conformal shapes for one or more lesions of the patient using a dynamic conformal arc (DCA) optimizer thereby calculating a first irradiation treatment;

using the calculated first irradiation treatment as initialisation of a volumetric intensity modulated arc therapy (VMAT) optimizer;

performing an optimization for the one or more lesions of the patient using the initialized VMAT optimizer; and wherein the VMAT optimizer keeps all determined conformal apertures conformal during the optimization.

2. The method according to claim 1:

wherein the determining step is carried out for at least one irradiation angle facilitated by a radiation treatment (RT) apparatus; and wherein an irradiation angle is defined by a combination of a patient table angle and a gantry angle.

3. The method according to claim 1:

wherein the determining step is dependent from at least one of a shape of the respective lesion of the one or more lesions of the patient;

an organ at risk (OAR) of the patient;

a previous result of this determining step for another irradiation angle, wherein an irradiation angle is defined by a combination of a patient table angle and a gantry angle; and one or more mechanical constraints or of an irradiation source of a radiation treatment (RT) apparatus:

proximity of other lesions from the repsective lesion; size of the respective lesion; and location of the respective lesion in a body of the patient.

4. The method according to claim 1, further including:

providing the VMAT optimizer with a dose prescription for said patient; and wherein the dose prescription defines prescribed dose values to be delivered to one or more of the lesions of the patient, and/or one or more dose limits for organs at risk/risk structures of the patient.

5. The method according to claim 1:

wherein the determining step is carried out by receiving a user input about the at least one or more lesions of the patient, and about information whether the at least one or more lesion is to be irradiated with conformal apertures or with modulated apertures.

6. The method according to claim 1:

wherein the determining step is carried by a computer-implemented method of automatically determining for the at least one or more lesions of the patient one or more conformal apertures to be used during radiation treatment; and wherein said automatic determination is based on data analysis of customer data, and/or is based on a simulation.

7. The method according to claim 1:

wherein the determining step is carried out before the optimization for the one or more lesions of the patient using the VMAT optimizer or wherein the determining step is carried out during the optimization for the one or more lesions of the patient using the VMAT optimizer.

8. The method according to claim 1:

wherein during the optimization step using the VMAT optimizer a second irradiation treatment is calculated.

9. The method according to claim 8, wherein the calculated second irradiation treatment uses at least one hybrid arc containing both conformal apertures of a Multi Leaf Collimator (MLC) of a radiation treatment (RT) apparatus and modulated apertures of the MLC of the RT apparatus.

10. The method according to claim 1:

wherein during the optimization step using the VMAT optimizer a respective dose distribution for the one or more lesions of the patient is optimized at the same time.

11. The method according to claim 1 wherein at each iteration of the optimization step using the VMAT optimizer the respective dose for the one or more lesion of the patient is known.

12. The method according to claim 1 wherein the initialisation of the VMAT optimizer contains a provision of initialized apertures based on a calculated first irradiation treatment; the method further comprising the step:

using, by the VMAT optimizer and during the optimization, the initialized apertures for further optimizing at least one of conformity, iso-dose line prescription of the one or more lesions at the same time, normal tissue dose and dose to risk structures, gradient index, treatment time, and modulation complexity.

13. The method according to claim 1, the method further comprising;

performing an arc setup optimization.

14. The method according to claim 13, wherein the arc setup optimization comprises:

acquiring a first arc setup comprising a plurality of arcs, each arc being defined by a combination of a patient table angle, a gantry start angle and a gantry stop angle;

distributing a plurality of target volumes, which describe the one or more lesions of the patient, to the arcs of the first arc setup thereby providing a packed first arc setup;

comparing said packed first arc setup with one or more predefined arc setup constraints;

wherein the one or more predefined arc setup constraints are selected from: a number of patient table angles per target volume, a number of passes, a sum of gantry span per metastasis over all arcs, a minimum table span, and a total number of patient table angles;

and the method further comprising:

automatically suggesting at least a second arc setup based on a result of the comparison; and using the suggested second arc setup during performing the treatment optimization based on conformal shapes using the DCA optimizer.

15. The method according to claim 14, wherein for each of the one or more predefined arc setup constraints a minimum and a maximum is defined.

16. The method according to claim 14, wherein a predefined arc setup constraint about the number of patient table angles defines a minimum number of patient table angles; and wherein, if a result of the comparison of the packed first arc setup with the one or more predefined arc setup constraints is that the minimum of the number of patient table angles is not violated, the method further comprises the step:

removing a patient table angle from the first arc setup; and/or wherein the predefined arc setup constraint about the number of passes defines a minimum number of passes; and wherein, if the result of the comparison of the packed first arc setup with the one or more predefined arc setup constraints is that the minimum of the number of passes is not violated, the method further comprises the step:

removing a pass from the first arc setup.

17. A non-transitory computer readable storage medium comprising instructions which, when executed by at least one processor, cause the at least one processor to:

determine for at least one or more lesion of a patient, one or more conformal apertures to be used during radiation treatment;

perform a treatment optimization based on conformal shapes for the one or more lesions of the patient using a dynamic conformal arc (DCA) optimizer thereby calculating a first irradiation treatment;

use the calculated first irradiation treatment as initialisation of a volumetric intensity modulated arc therapy (VMAT) optimizer;

perform an optimization for the one or more lesions of the patient using the initialized VMAT optimizer; and wherein the VMAT optimizer keeps all determined conformal apertures conformal during the optimization.

18. A medical system, comprising:

at least one processor;

at least one electronic data storage device storing at least patient data describing multiple lesions of a patient; and a medical device for carrying out a medical procedure on the patient, wherein the at least one processor is operably coupled to:

the at least one electronic data storage device for acquiring, from the at least one electronic data storage device, the patient data describing the multiple lesions of the patient, the at least one processor operable to:

perform an optimization for the multiple lesions of the patient using an initialized volumetric intensity modulated arc therapy (VMAT) optimizer; and wherein the VMAT optimizer keeps all determined conformal apertures conformal during the optimization; and issuing a control signal to the medical device for controlling an operation of the medical device on a basis of a result of the optimization.

19. The medical system according to claim 18, wherein the medical device comprises:

a radiation treatment (RT) apparatus comprising a treatment beam source and a patient support unit;

wherein the at least one processor is operably coupled to a radiation treatment apparatus for issuing a control signal to the radiation treatment apparatus for controlling, on the basis of a result of the optimization, at least one of:

the operation of the treatment beam source, or the position of the patient support unit.

* * * * *